(12) United States Patent
Kosinski et al.

(10) Patent No.: US 6,790,197 B2
(45) Date of Patent: Sep. 14, 2004

(54) SINGLE USE SYRINGE AND PLUNGER ROD LOCKING DEVICE THEREFOR

(75) Inventors: Anthony J. Kosinski, New Providence, NJ (US); Gene Fleischer, New City, NY (US); Marcos Calucho, Fraga (ES)

(73) Assignee: Becton Dickinson and Company, Franklin Lakes, NJ (US)

(*) Notice: Subject to any disclaimer, the term of this patent is extended or adjusted under 35 U.S.C. 154(b) by 162 days.

(21) Appl. No.: 10/254,264

(22) Filed: Sep. 25, 2002

(65) Prior Publication Data

US 2004/0059300 A1 Mar. 25, 2004

(51) Int. Cl.⁷ .............................................. A61M 5/00
(52) U.S. Cl. ..................... 604/110; 604/218; 604/222
(58) Field of Search .............................. 604/110, 210, 604/181, 187, 218–222, 239–243, 224, 236, 238

(56) References Cited

U.S. PATENT DOCUMENTS

| | | | |
|---|---|---|---|
| 4,367,738 A | 1/1983 | Legendre et al. | 128/218 |
| 4,386,606 A | 6/1983 | Tretinyak et al. | 604/220 |
| 4,731,068 A | 3/1988 | Hesse | 604/110 |
| 4,758,232 A | 7/1988 | Chak | 604/220 |
| 4,781,683 A | 11/1988 | Wozniak et al. | 604/110 |
| 4,781,684 A | 11/1988 | Trenner | 604/110 |
| 4,826,483 A | 5/1989 | Molnar, IV | 604/110 |
| 4,840,616 A | 6/1989 | Banks | 604/110 |
| 4,961,728 A | 10/1990 | Kosinski | 604/110 |
| 4,973,310 A | 11/1990 | Kosinski | 604/110 |
| 4,978,339 A | 12/1990 | Labouze et al. | 604/110 |
| 5,000,737 A | 3/1991 | Free et al. | 604/110 |
| 5,205,825 A | 4/1993 | Allison et al. | 604/110 |
| 5,215,536 A | 6/1993 | Lampropoulos et al. | 604/220 |
| 5,222,942 A | 6/1993 | Bader | 604/110 |
| 5,250,030 A | 10/1993 | Corsich | 604/110 |
| 5,733,261 A | 3/1998 | Obong | 604/110 |
| 5,814,017 A | 9/1998 | Kashmer | 604/110 |
| 5,989,219 A | 11/1999 | Villas et al. | 604/110 |
| 6,217,550 B1 | 4/2001 | Capes | 604/110 |
| 6,283,941 B1 * | 9/2001 | Schoenfeld et al. | 604/110 |
| 6,494,863 B1 | 12/2002 | Shaw et al. | 604/110 |
| 6,599,269 B1 * | 7/2003 | Lewandowski et al. | 604/110 |
| 2003/0060759 A1 * | 3/2003 | Lau et al. | 604/110 |

* cited by examiner

Primary Examiner—Brian L. Casler
Assistant Examiner—Cris L. Rodriguez
(74) Attorney, Agent, or Firm—Jeanne P. Lukasavag; John L. Voellmicke

(57) ABSTRACT

A single use syringe and a plunger rod locking device for such a syringe are provided. The locking device and plunger rod include features that cause the plunger rod to be locked with respect to the syringe barrel upon completion of an injection stroke. A cutting member is provided at the distal end of the locking device. The cutting member will penetrate, and thereby disable the stopper affixed to the plunger rod in an attempt to retract the plunger rod following the injection stroke. The locking device includes barbs for engaging the syringe barrel.

36 Claims, 13 Drawing Sheets

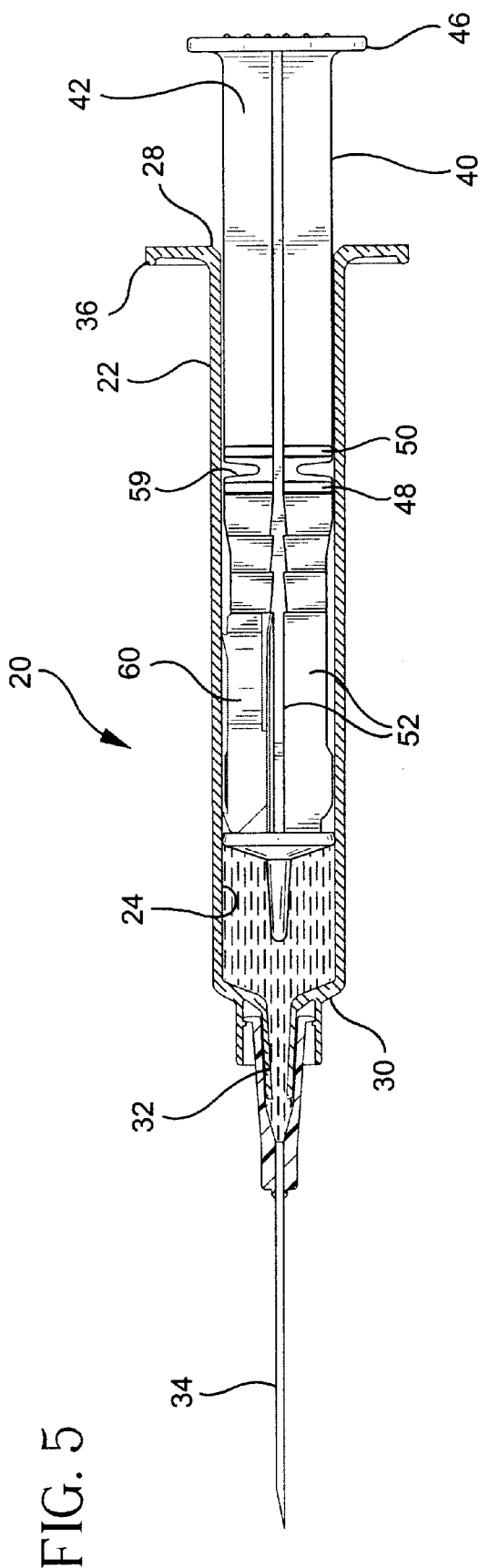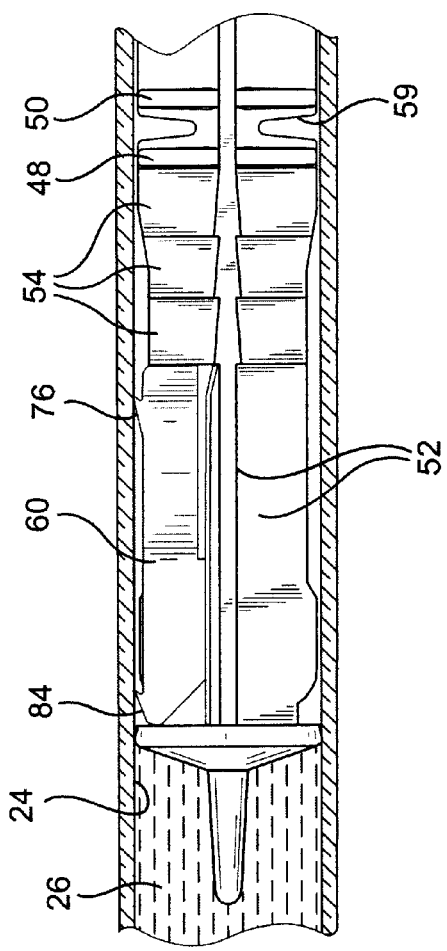
FIG. 5
FIG. 5A

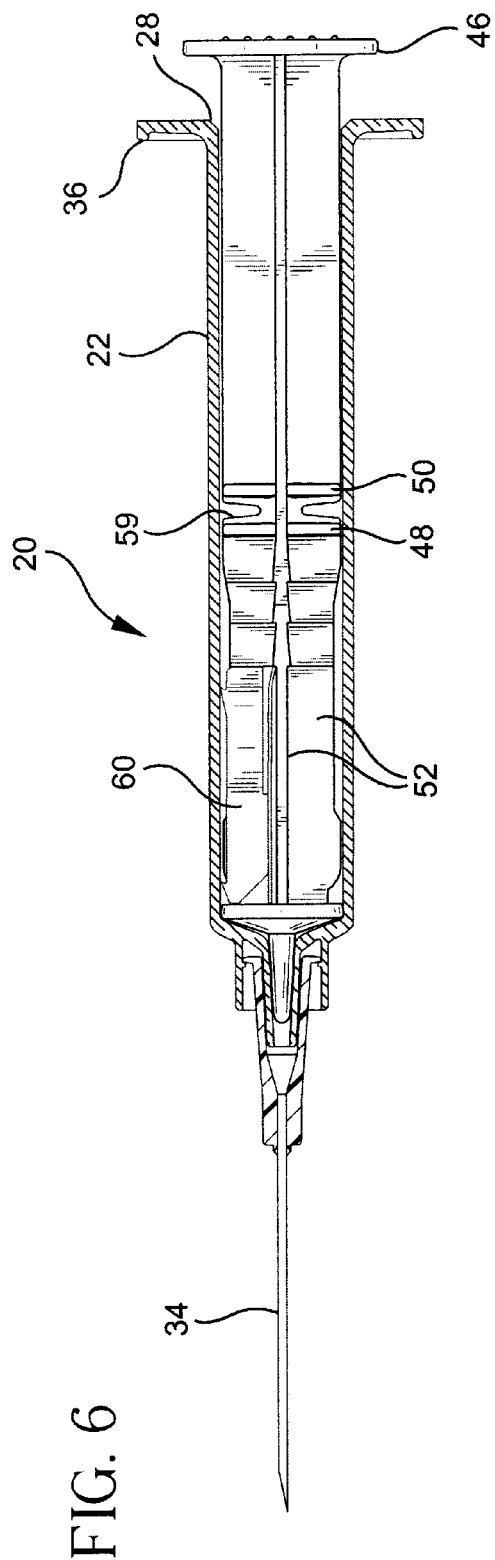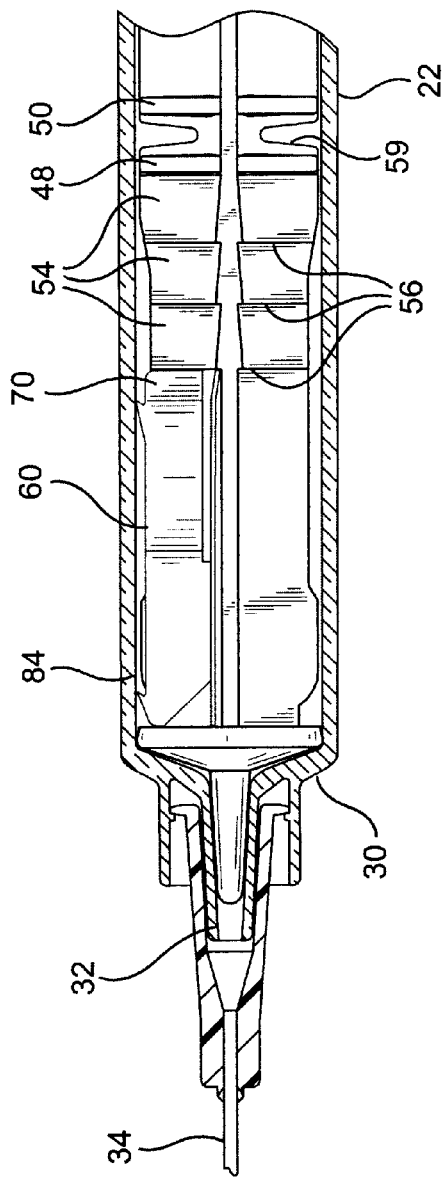
FIG. 6
FIG. 6A

SINGLE USE SYRINGE AND PLUNGER ROD LOCKING DEVICE THEREFOR

BACKGROUND OF THE INVENTION

1. Field of the Invention

The field of the invention relates to single use syringes and locking devices for locking the plunger assemblies of such syringes.

2. Brief Description of the Related Art

In the United States and throughout the world the multiple use of hypodermic syringe products that are intended for single use only is instrumental in drug abuse and more particularly in the transfer of diseases. Intravenous drug users who routinely share and reuse syringes are a high risk group with respect to the AIDS virus. Also, the effects of multiple use are a major concern in developing countries where repeated use of syringe products may be responsible for the spread of many diseases.

Many syringes have been made to remedy this problem. Some of these have required a specific act to destroy the syringe after use either by using a destructive device or providing a syringe assembly with frangible zones so that the syringe could be rendered inoperable by the application of force. Other syringes include structure which allows the destruction or defeating of the syringe function through a conscious act by the syringe user. Although many of these devices work quite well, they do require the specific intent of the user followed by the actual act to destroy or render the syringe inoperable. None of these devices is effective with a user having the specific intent to reuse the hypodermic syringe.

Single use hypodermic syringes that become inoperative or incapable of further use automatically without any additional act on the part of the user have been developed. One such syringe is disclosed in U.S. Pat. No. 4,961,728. The syringe disclosed in this patent includes a locking element positioned in the syringe barrel. The locking element includes proximally and outwardly facing barbs that engage the inner surface of the syringe barrel and an inwardly facing driving edge adapted to interact with the plunger rod to move the locking element along the barrel as the stopper is advanced. The plunger rod includes a ledge positioned at a distance from the proximal side of a support wall that approximates the length of the locking element. The driving edge of the locking element engages the ledge, thereby ensuring that the locking element moves distally with the plunger rod and stopper. A syringe including a similar locking element is disclosed in U.S. Pat. No. 5,989,219.

U.S. Pat. Nos. 5,021,047, 5,062,833 and 5,562,623 disclose single use syringes having plunger rods that have teeth or ridges and locking elements that engage the teeth or ridges. The locking elements of these syringes also include outwardly extending teeth or prongs that engage the inside surface of the syringe barrel. The plunger rods of these syringes can be retracted to draw fluid into the syringe barrel while the locking elements remain stationary. Distal movement of the plunger rods causes the fluid to be expelled, the locking elements moving distally with the plunger rods with the intention of preventing further plunger rod retraction.

Although the prior art provides syringes having locking elements that will automatically lock the syringe barrel and plunger rod to help prevent re-use, there is still a need for additional features that will cause the destruction of the syringe's functionality if excessive force is used to withdraw the plunger rod after injecting medication.

SUMMARY OF THE INVENTION

A locking element for locking a syringe plunger rod having a stopper, with respect to a syringe barrel and for rendering a stopper unusable is provided by the invention. The locking element includes a body portion having distal and proximal end portions. First and second means are provided on the body portion for engaging a plunger rod and syringe barrel, respectively, such that the locking element can slide distally, but not proximally, with respect to the syringe barrel. One or more cutters are attached to, and preferably integral with the distal end portion are provided for cutting the stopper if excessive force is applied to the plunger rod. The cutter may be formed by a cutting edge.

The invention further relates to a syringe assembly including a locking element capable of locking a plunger rod with respect to a syringe barrel and rendering a stopper unusable. The assembly includes a syringe barrel, a plunger rod, a locking element and a cutter. The syringe barrel includes an inside surface defining a chamber, an open end, and a distal end. The plunger rod assembly includes an elongate body portion and a stopper. The locking element is slidably-positioned within the chamber of the syringe barrel, engaging the inside surface thereof such that the locking element is substantially immovable in the direction of the open end of the syringe. It is also engageable with the plunger rod assembly such that the plunger rod assembly and locking element can be moved distally together toward the distal end of the syringe barrel. In a preferred embodiment, the plunger rod assembly can initially be moved proximally with respect to the locking element to aspirate fluid into the syringe barrel. A cutter is connected to the locking element and is engageable with the stopper. The cutter is capable of cutting the stopper upon attempted withdrawal of the plunger rod assembly from the syringe barrel.

A further embodiment of a locking element for a single use syringe having a plunger rod with a stopper is also provided. The locking element includes a distal portion and a proximal portion. The distal portion includes a generally V-shaped body comprising first and second walls connected along a longitudinal axis. A first leg extends proximally from the first wall of the body. A second leg extends proximally from the second wall of the body, and is separated from the first leg by a gap. Each leg includes one or more barbs. A cutting member is provided on a distal portion of the locking element. One or more barbs may also be provided on the distal portion of the locking element. This portion preferably further includes a pair of distally extending legs. The barbs are preferably integral with the distal ends of the distally extending legs.

A further single use syringe assembly in accordance with the invention includes a barrel having an inside surface defining a chamber for retaining fluid. The barrel has an open proximal end and a distal end having a passageway in communication with the chamber. A plunger rod assembly is provided for use in conjunction with the barrel. The plunger rod assembly includes an elongate body portion having a proximal end, a distal end, and a stopper mounted to the elongate body portion proximate the distal end. The stopper is slidably positioned in substantially fluid tight engagement with the inside surface of the barrel. The elongate body portion of the plunger rod assembly extends outwardly from the open proximal end of the barrel. It includes at least one elongate recess. A plurality of steps or teeth are provided within the recess. A locking element is positioned within the barrel. One or more proximally facing barbs extend from the locking element. The barbs engage the inside surface of the barrel for substantially preventing the locking element from moving proximally with respect to the barrel. The locking element also engages the elongate body portion of the plunger rod assembly such that the locking element is movable towards the distal end of the barrel as the plunger rod assembly is advanced. Each tooth defines a distally facing surface that is engageable by a proximal edge of the locking element. A cutting member is provided on the distal end of the locking element.

A single use syringe assembly is further provided that includes a barrel having an inside surface defining a chamber for retaining fluid, a plunger rod assembly, and a locking element. The plunger rod assembly includes an elongate body portion having a proximal end, a distal end and a stopper mounted to the elongate body portion. The stopper is slidably positioned in substantially fluid tight engagement with the inside surface of the barrel. The locking element is positioned within the barrel. It includes a generally V-shaped body comprising first and second walls connected along a longitudinal axis. A first leg extends proximally from the first wall and a second leg extends proximally from the second wall. A first barb extends from the first leg of the locking element while a second barb extends from the second leg thereof. It will be appreciated that one or more barbs may extend from the legs of the locking element. Each leg includes an end portion engageable with the body portion of the plunger rod assembly. The locking element preferably includes proximally facing barbs near the distal end of the V-shaped body, preferably extending from a pair of legs integral with the V-shaped body. The locking element can accordingly be moved distally with the plunger rod assembly along the syringe barrel. The barbs substantially prevent the locking element from moving proximally therein. A cutting member is provided at the distal end of the V-shaped body for cutting the stopper.

BRIEF DESCRIPTION OF THE DRAWINGS

FIG. 5 is a cross-sectional view thereof showing the syringe assembly following retraction of the plunger rod assembly to fill the syringe;

FIG. 5A is an enlarged cross-sectional view of the distal end thereof;

FIG. 6 is a cross-sectional view thereof showing the plunger rod assembly in a locked position following the injection stroke;

FIG. 6A is an enlarged cross-sectional view of the distal end thereof;

DETAILED DESCRIPTION OF THE INVENTION

Figure 1:
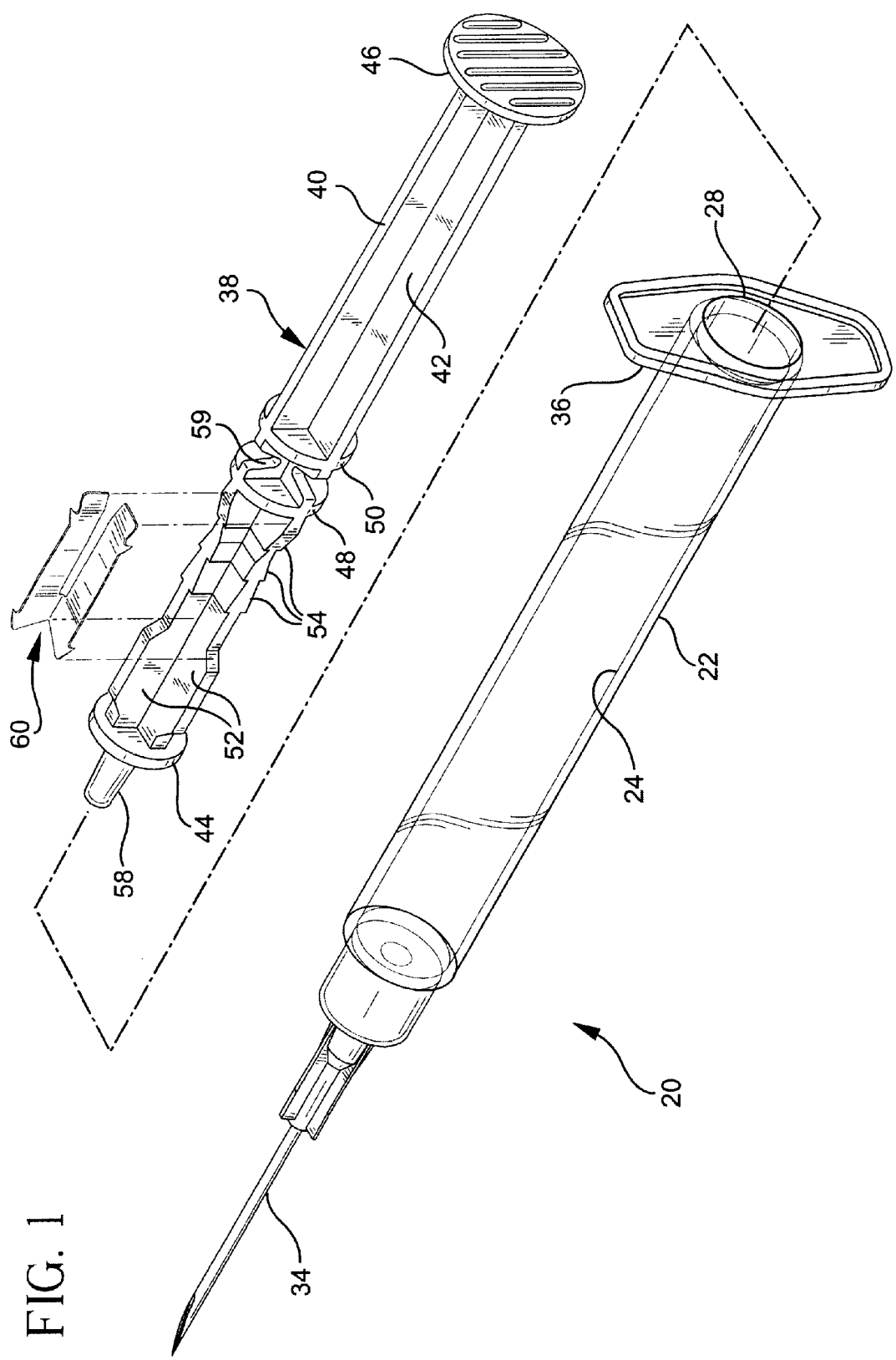
FIG. 1 is an exploded, perspective view showing a single use syringe assembly of the invention.

There is shown in the drawings and will be described in detail herein a preferred embodiment of the invention with the understanding that the present disclosure is to be considered as exemplary of the principles of the invention and is not intended to limit the invention to the embodiment illustrated.

Referring first to FIGS. 1–7, a single use syringe assembly 20 includes a barrel 22 having an inside surface 24 defining a chamber 26 for retaining fluid. The barrel 22 includes an open end 28 and a distal end 30 having a passageway 32 therethrough in communication with the chamber. A needle cannula 34 projects outwardly from the distal barrel end. The needle cannula has a lumen (not shown) therethrough in fluid communication with the passageway and a sharpened distal tip. The syringe assembly of this embodiment is shown with a needle cannula assembly that is removably attached to the distal end of the barrel. It is also a purview of the present invention to include syringe barrels having permanently affixed needles or needle hub assemblies, or fixed or removable blunt cannulas.

As used in the preceding paragraph and hereafter, the term "distal end" refers to the end furthest from the person holding the syringe assembly. The term "proximal end" refers to the end closest to the holder of the syringe assembly. In the preferred embodiment, the proximal end of the barrel 22 includes a flange 36 to facilitate handling and positioning of the syringe assembly and to maintain the relative position of the barrel with respect to the plunger rod during medication filling and administration.

Figure 8:
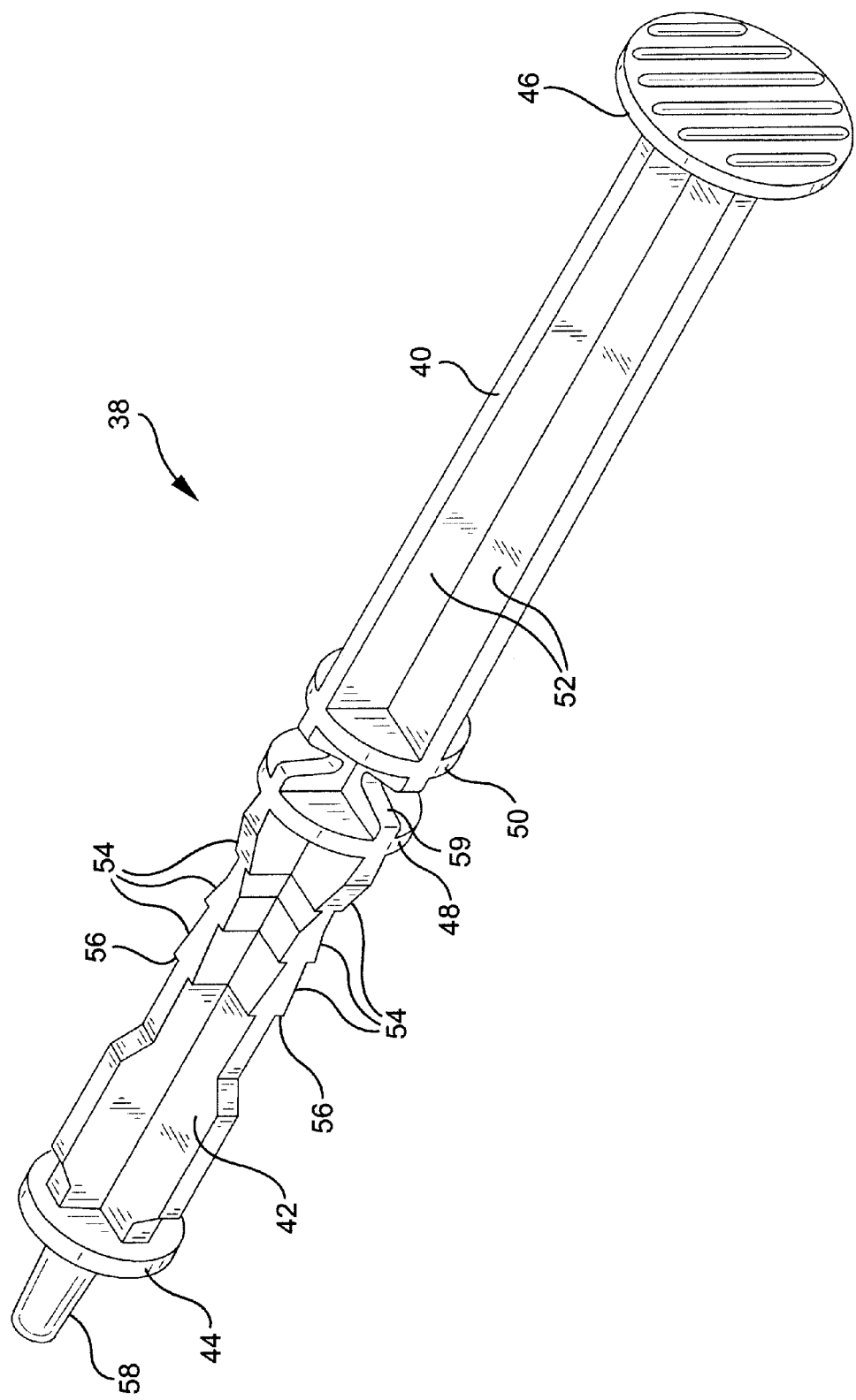
FIG. 8 is a top perspective view of the plunger rod assembly for the single use syringe assembly.
Figure 9:
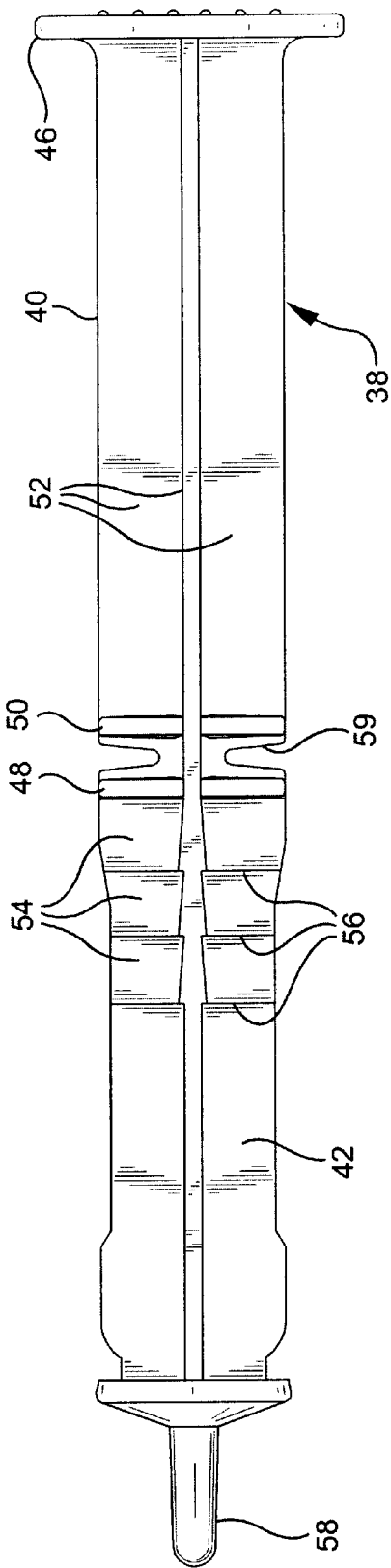
FIG. 9 is a side elevation view of the plunger rod assembly.
Figure 10:
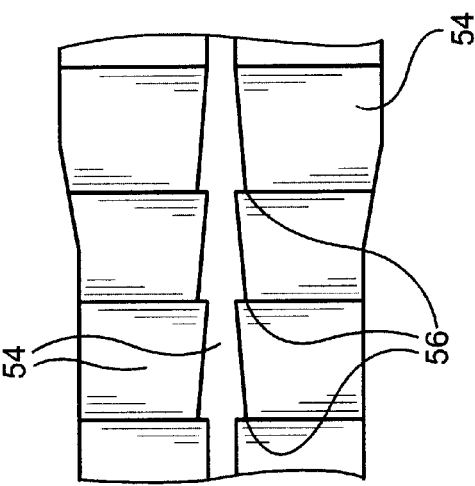
FIG. 10 is an enlarged side elevation view of a portion of the plunger rod assembly.
Figure 11:
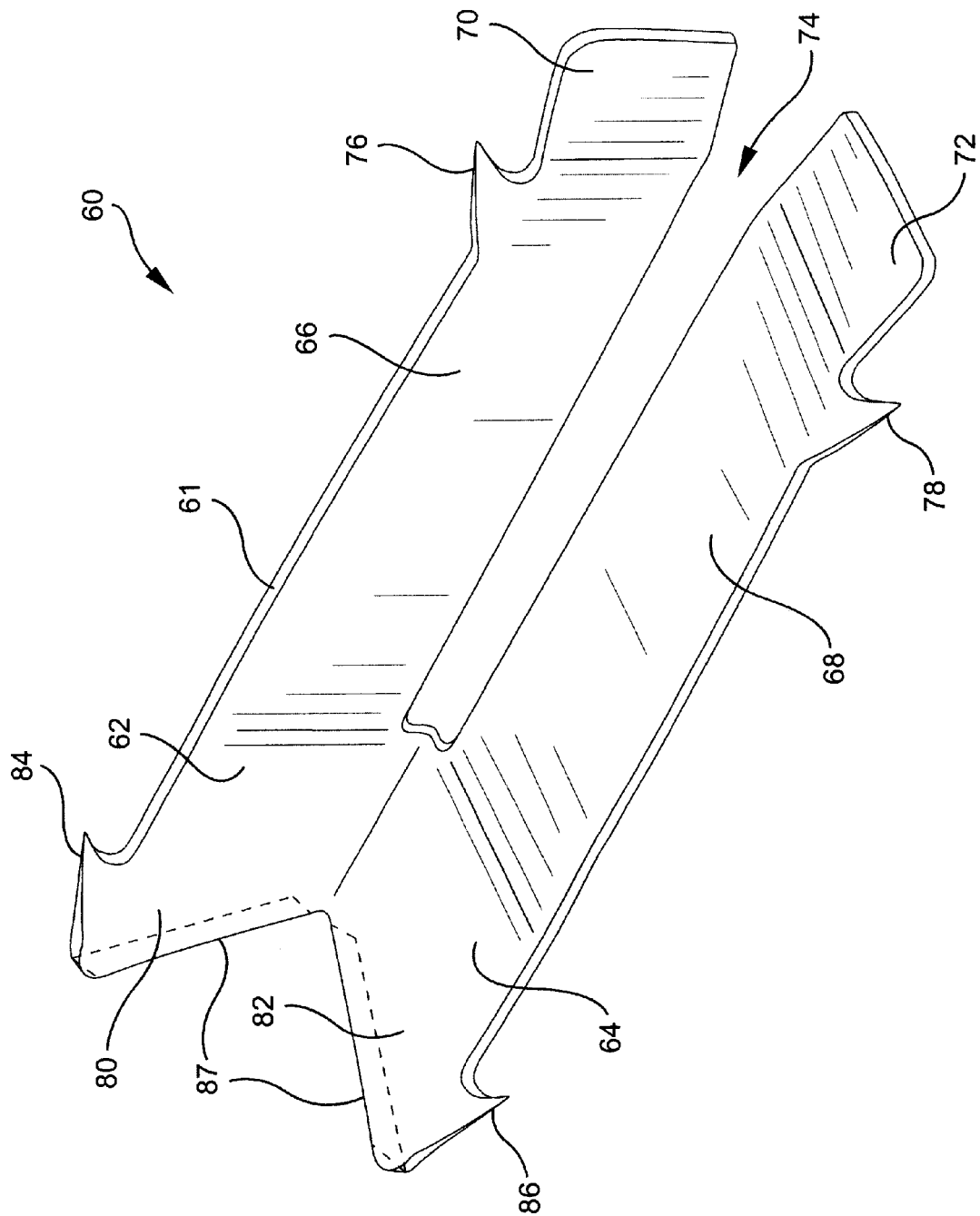
FIG. 11 is a perspective view of a locking element in accordance with a preferred embodiment of the invention.
Figure 12:
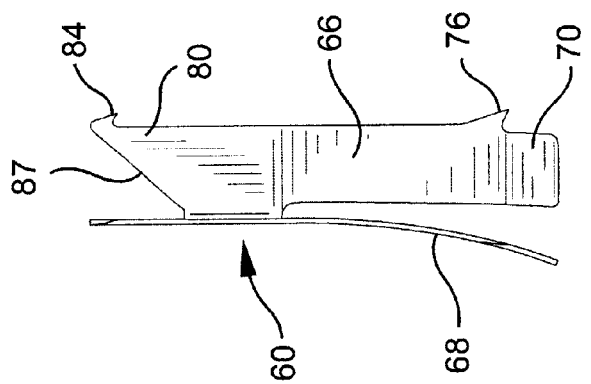
FIG. 12 is a top plan view of a preform of the locking element.
Figure 13:
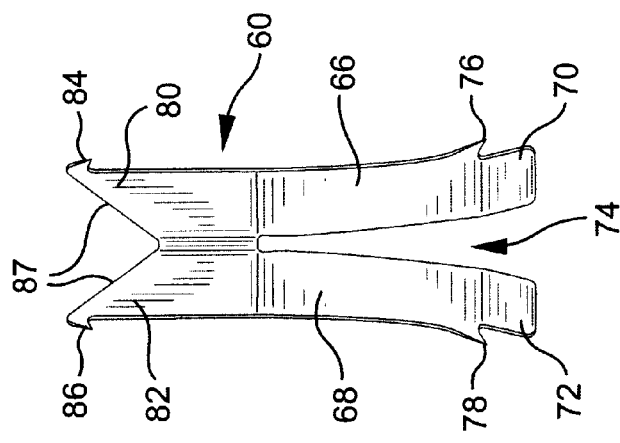
FIG. 13 is a top plan view of the locking element.

A plunger rod assembly 38 used in the syringe assembly 20 includes an elongate body portion 40 including at least one and preferably a plurality of elongate recesses 42. The distal end of the elongate body portion includes an integral stopper 44. A disc-shaped flange 46 is provided at the proximal end of the plunger rod for allowing the user to apply the force necessary to move the plunger rod with respect to the barrel. The elongate body portion 40 includes a pair of discs 48, 50 intermediate the proximal and distal ends thereof. The section between the relatively proximal disc 50 and the flange 46 and the two discs 48, 50 include radially extending walls 52 that define portions of the elongate recesses 42. The section adjoining the relatively distal disc 48 has radially extending walls 52 that define one or more ratchet-like teeth 54. Each tooth 54 includes a distally facing surface or shoulder 56, as best shown in FIGS. 8–10. A frustoconical nose portion 58 forms the distal end of the plunger rod assembly. It will be appreciated that while the plunger rod assembly as shown and described herein is of integral construction, it may in fact be comprised of two or more separate elements. The stopper may, for example, be a separate component made from a material that is different from the material comprising the remainder of the plunger rod assembly, such as a flexible stopper, O-ring or the like.

A locking element 60 is positioned within barrel 22 and within elongate recess 42 in the plunger rod assembly 38. The recess 42 acts as a pathway for longitudinal motion of the locking element relative to the plunger rod assembly.

Figure 14:
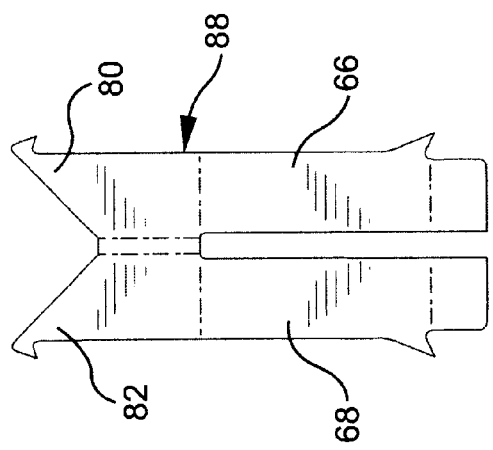
FIG. 14 is a side elevation view of the locking element.
Figure 16:
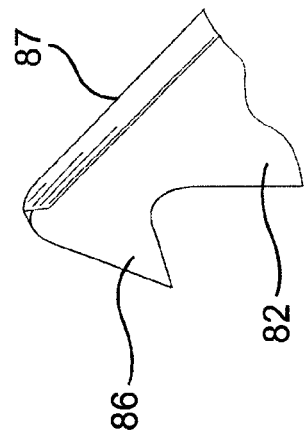
FIG. 16 is an enlarged view of a cutting edge at the distal end of the locking element.

The locking element 60, as best shown in FIGS. 11–15, includes a generally V-shaped body portion 61 comprising first and second radially extending walls 62, 64 joined along a longitudinal axis. A first leg 66 extends proximally from the first wall and a second leg 68 extends proximally from the second wall 64. The legs flare outwardly with respect to the V-shaped body portion 61, as best shown in FIG. 14. The legs 66, 68 are preferably longer than the length of the body portion 61. In a locking element having an overall length of about seventeen millimeters, the legs 66, 68 may be about ten millimeters in length.

Each of the legs 66, 68 include a proximal end portion 70, 72 that is angled toward one of the radially extending walls 52 of the plunger rod assembly. They further include inner and outer edges. (The terms "inner" and "outer" are relative terms as used herein.) The inner edges thereof are substantially adjacent to each other, separated by a longitudinal gap 74. Barbs 76, 78 are integral with the outer edges of the first and second legs. The barbs face proximally, and are preferably located slightly distally of the angled end portions 70, 72. The barbs may be different in appearance from those shown in the drawings so long as they are capable of engaging the inside surface 24 of the syringe barrel to prevent proximal movement of the locking element.

In this embodiment, a second pair of legs extends distally from the V-shaped body portion 61. One of these legs 80 extends from the first wall 62 and the other 82 from the second wall 64. Legs 80 and 82 preferably include barbs 84 and 86 respectively. Barbs 84, 86 extend proximally from the distal ends of the legs 80, 82. The barbs are formed on the outer edges of the distally extending legs. Each leg further includes a cutting edge 87 capable of penetrating the stopper 44. As used herein the term cutting edge or cutter is intended to include cutting edges and/or pointed projections or any other structure capable of cutting through or piercing the stopper.

Figure 15:
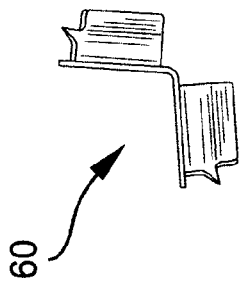
FIG. 15 is an end view of the locking element.

The locking element is preferably formed from a thin sheet of metal such as stainless steel. The thickness in the preferred embodiment is about 0.20 mm. The locking element is preformed into the flat configuration shown in FIG. 12. The broken lines show where the folds will be made in the flat substrate 88 to form the locking element 60 shown in FIGS. 11 and 13–15. The dimensions of the locking element are selected in accordance with the barrel and plunger rod assembly with which it is to be used. The angle formed between the two halves of the locking element in this embodiment, as shown in FIG. 15, is desirably about 90 degrees, and preferably about 100 degrees. When placed in one of the recesses 42 in the plunger rod assembly, the locking element will accordingly exert a force against the two adjoining walls 52 that define the recess. At least one cutting edge is preferably formed by providing a bevel on one side of the substrate. The preferred embodiment contains two cutting edges 87. It will be appreciated that the substrate could be worked by grinding or other means on both sides thereof to form cutting edges for disabling the stopper 44. Alternatively, a distally extending barb on leg 80 and/or leg 82 or other cutting member can be provided on the locking element for piercing or cutting the stopper.

Figure 2:
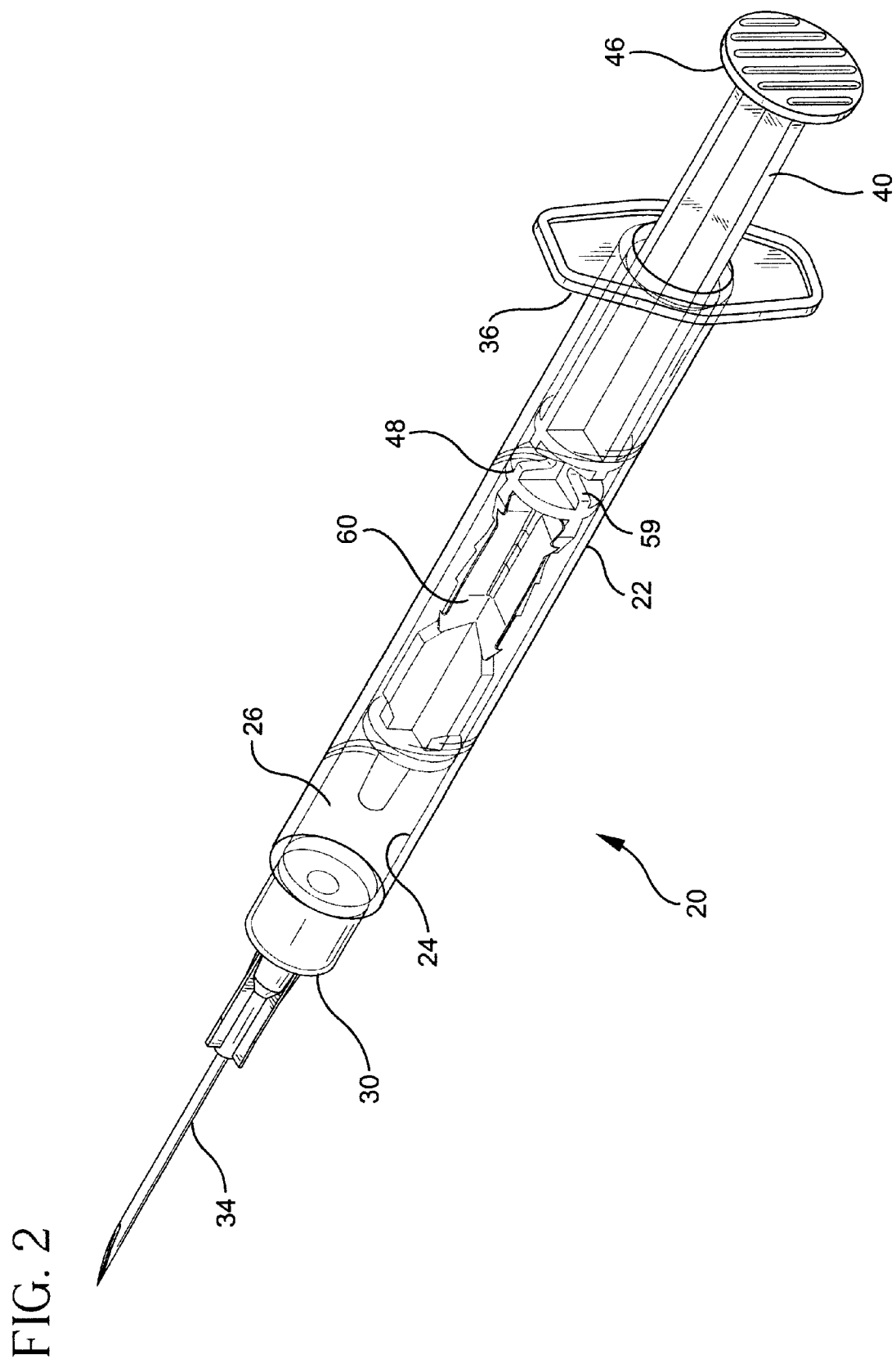
FIG. 2 is a top perspective view showing a step in the manufacture of the syringe assembly.
Figure 3:
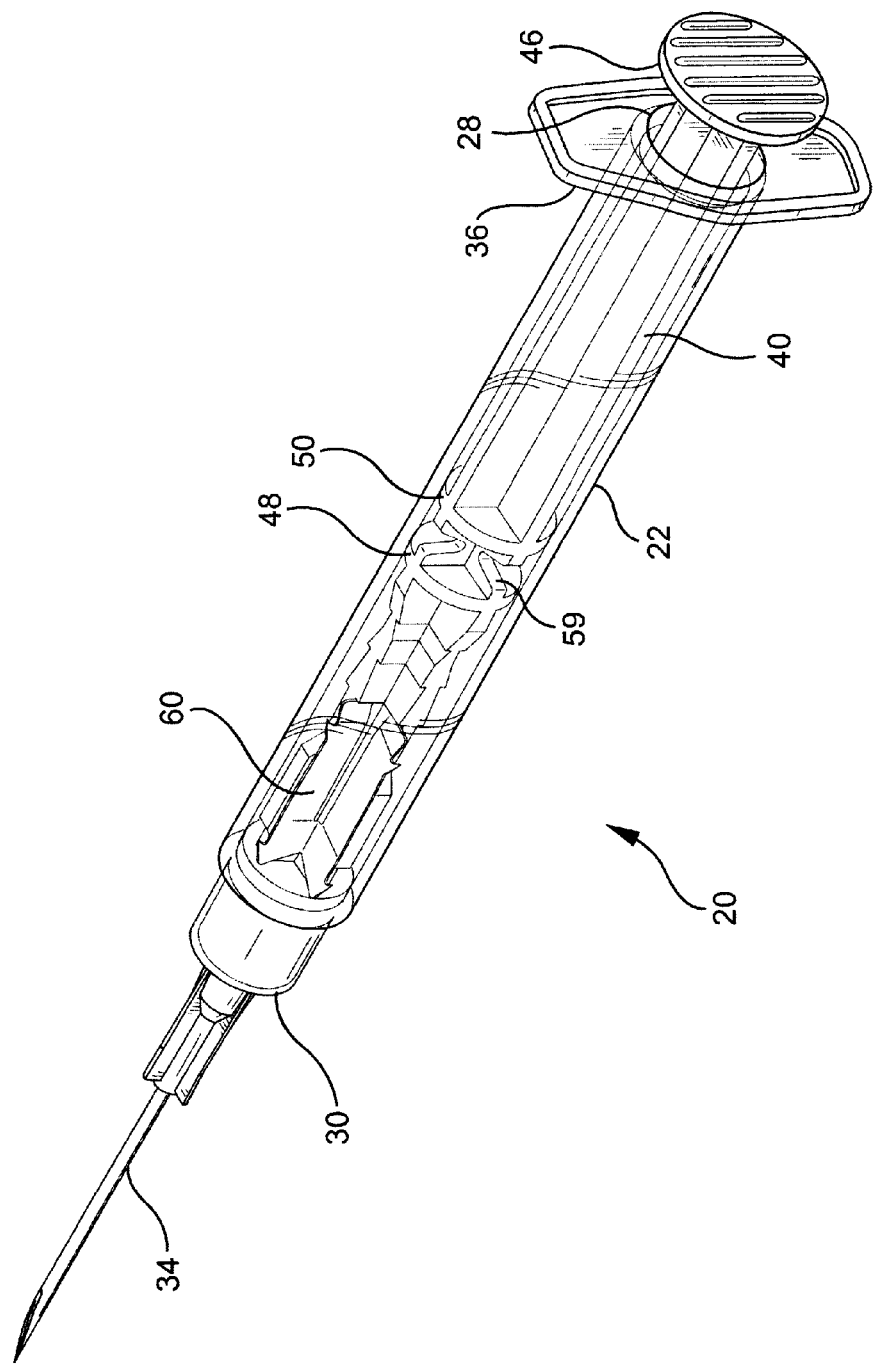
FIG. 3 is a top perspective view thereof showing the syringe assembly following the injection stroke of the plunger rod assembly thereof.
Figure 4:
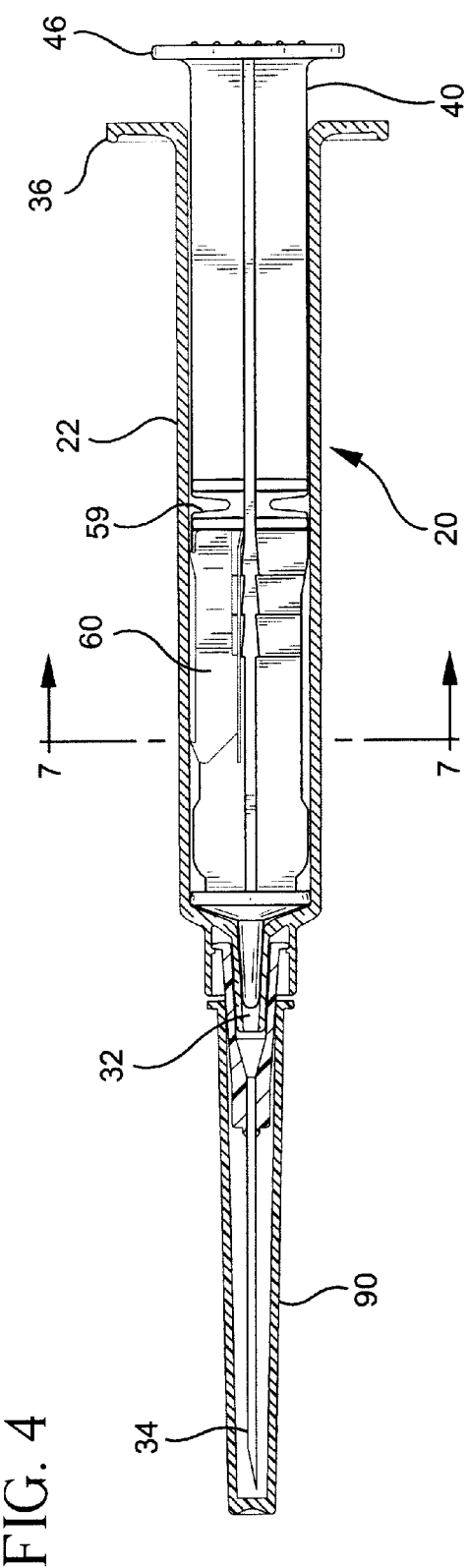
FIG. 4 is a cross-sectional view of the syringe assembly with the plunger rod assembly in a position prior to use.
Figure 4A:
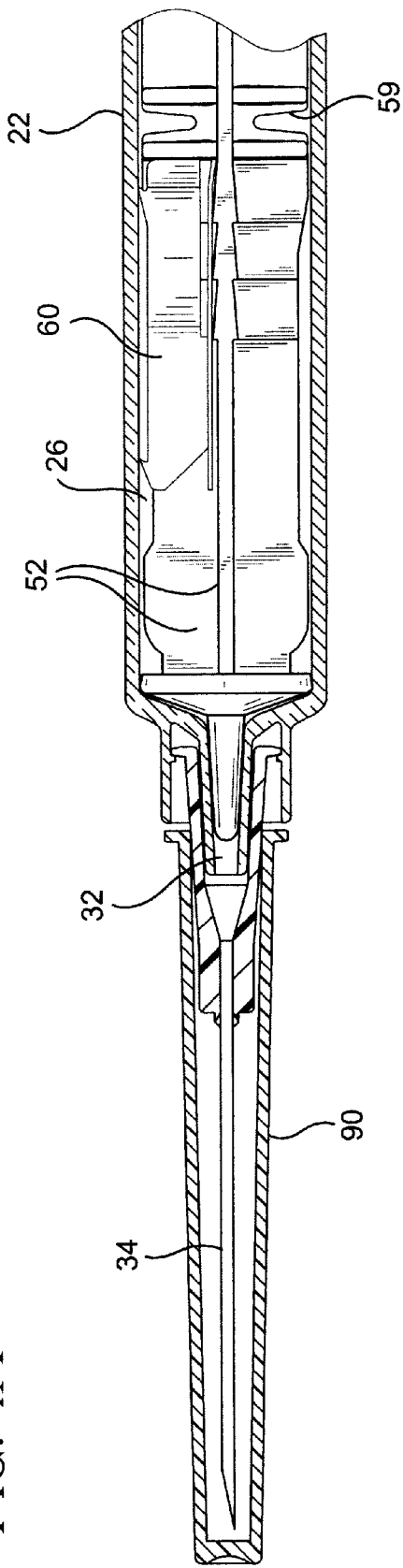
FIG. 4A is an enlarged cross-sectional view of the distal end thereof.
Figure 7:
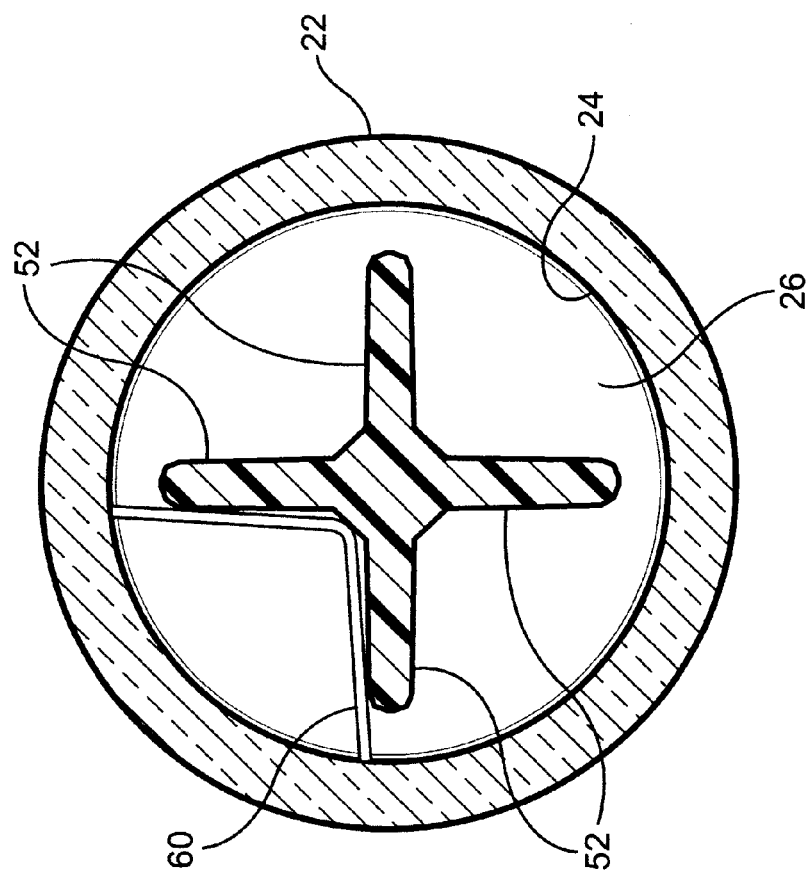
FIG. 7 is a cross-sectional view taken along line 7—7 of FIG. 4.

The syringe assembly is easily constructed from the component parts thereof. Locking element 60 is positioned in one of the recesses 42 in the plunger rod assembly such that the angled end portions of legs 66, 68 adjoin the relatively distal disk 48, as shown in FIG. 1. Legs 66, 68 and spring member extend proximally, and barbs 76, 78, 84, 86 are angled proximally with respect to the plunger rod assembly. The plunger rod/locking element assembly is then inserted into barrel 22 through the proximal end thereof. As the assembly is moved distally within the barrel, the angular orientation of the barbs allows them to slide along while engaging inside surface 24 of the barrel. The locking element moves distally with the plunger rod due to the engagement of the ends of the legs 66, 68 with disc 48. Gap 74 is maintained between the legs 66, 68 even after installation of the locking element. The maintenance of the gap acts as a cantilever spring, provide a relatively reduced force on the barrel and facilitate use and installation. The plunger rod/locking element assembly is moved distally, as shown in FIG. 2 until the stopper engages the end wall of the barrel as shown in FIG. 4. It is then ready for use or storage. A needle cover 90 can be mounted to the distal end of the barrel to protect the needle cannula. The cover is removed prior to use.

In use, plunger rod assembly 38 is retracted from the position shown in FIG. 4 to the position shown in FIG. 5 in order to draw fluid through needle cannula 34 and passageway 32 and into chamber 26 of barrel 22. Locking element 60 remains stationary during such retraction, and the plunger rod assembly is moved proximally with respect to both barrel 22 and the locking element. This is due to the engagement of the barbs 76, 78, 84, 86 with the inside surface 24 of the barrel. Although this preferred embodiment illustrates four barbs, the locking element can function with more barbs or as few as one barb. The number and placement of the barbs is chosen to enhance performance. In this embodiment it is believed that distal barbs 84 and 86 stabilize the cutting edge to help it cut the stopper. The barbs are preferably made from a harder material than the barrel, which enhances their ability to resist proximal movement. The angled ends 70, 72 of the legs 66, 68 of the locking element ride over the teeth 54 of the plunger rod assembly during retraction thereof. The multiple teeth are intended to prevent recycling the plunger rod in mid-stroke. The user may feel and/or hear the movement of the legs over the teeth.

Retraction of the plunger rod assembly 38 is limited by the locking element. As shown in FIGS. 5 and 5A, the proximal surface of the stopper 44 engages the distal end of locking element 60. The user can feel this engagement. Cutting edges 87 do not penetrate the stopper as a result of the forces exerted during normal use. As the locking element cannot be moved proximally, further retraction of the plunger rod assembly is not possible without applying extra force that would damage the stopper by allowing the cutting edges to cut the stopper. This is an important aspect of the present invention. The amount of fluid that can be drawn into the chamber 26 is accordingly limited by the distance between the proximal surface of the stopper and the disc 48 as well as the length of the locking element. It will be appreciated that the distance between the stopper and the relatively distal disc 48 and the length of the locking element 54 can be chosen to meet the needs of particular applications such as fill volumes of 0.01 ml, 0.05 ml, 0.5 ml, 1.0 ml and 2.0 ml.

The proximal end portions of the legs 66, 68 of the locking element preferably adjoin the end of the most distal tooth 54 when the plunger rod assembly is retracted to the position shown in FIG. 5. The distance between this end of the tooth 54 and the distal end surface of the relatively distal disc 48, being substantially the same as the distance between the distal end of the locking element and the proximal end portions of the legs, causes the locking element to be substantially immovable with respect to the plunger rod assembly. As discussed above, the locking element is substantially immovable in the proximal direction within the barrel due to the engagement of one or more barbs with the inside surface of the barrel 22. The syringe can be provided to the end user as a prefilled syringe, in which case retraction of the plunger rod assembly would not be necessary or possible.

Once the fluid has been drawn into the barrel from a vial or other fluid source, the needle cannula can be removed from the fluid source and used for injection. During the injection of a patient, the plunger assembly 38 and locking element both move distally from the positions shown in FIGS. 5 and 5A to the positions shown in FIGS. 6 and 6A. In FIGS. 6 and 6A, stopper 44 again adjoins or engages the end wall of barrel 22. The locking element remains positioned between disc 48 and most distal ratchet tooth 54. Both the plunger rod assembly 38 and the locking element are substantially immovable from their positions. The syringe assembly 20 accordingly cannot be reused. Should a person use extraordinary force in an attempt to retract the plunger rod assembly from the position shown in FIGS. 6 and 6A, cutting edges 87 at the distal end of the locking element will penetrate the stopper, rendering it unusable. Disabling of the stopper preferably occurs when the force exerted is sufficient to dislodge the locking element in the proximal direction, or a slightly lesser force. As discussed above, simple engagement of the cutting edges and stopper should not compromise the integrity of the stopper.

Cut-outs 59 are provided on the elongate body portion 40 of the plunger rod to produce a reduced cross-sectional area in the plunger rod. This reduced cross-sectional area is weak enough to break upon application of excessive bending or rotational force applied to the plunger rod in an attempt to re-use the syringe assembly.

The syringe barrel of the present invention may be constructed of a wide variety of thermoplastic materials such as polypropylene, polyethylene and combinations thereof being preferred. Similarly, thermoplastic materials such as polypropylene, polyethylene and polystyrene are preferred for the plunger rod and integral stopper. A wide variety of materials such as natural rubber, synthetic rubber and thermoplastic elastomers are suitable for the stopper if the stopper is manufactured as a separate component or made by a two-shot molding process or the like. The choice of stopper material will depend on compatibility with the medication being used and the barrel material and thickness since the stopper must form a seal with the inside surface of the barrel to deliver medication through the needle cannula.

As previously recited, it is preferable that the locking element be fabricated from a material which is harder than the barrel so that the locking barbs may effectively engage the barrel. Resilient spring like properties are also desirable along with low cost, dimensionally consistent fabrication. With this in mind, sheet metal is a desirable material for the locking element with stainless steel being preferred. Although the locking element of the preferred embodiment is fabricated from a single sheet, it is within the purview of the instant invention to include locking elements made of other forms and/or containing multiple parts. Locking elements having structures other than that shown and described herein could also be successfully employed. Alternatively, one or more distally extending barbs could be provided at the distal end of the locking element for rendering the stopper unusable.

Figure 18:
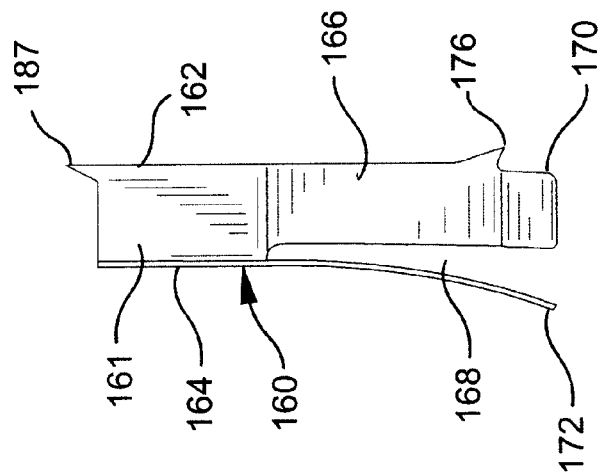
FIG. 18 is a side elevation view of the locking element of FIG. 17.
Figure 17:
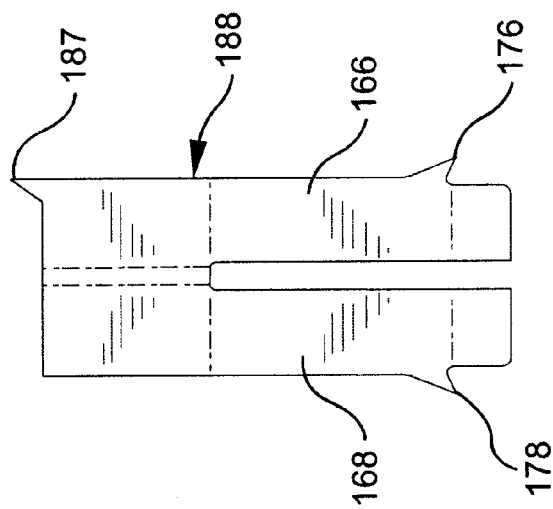
FIG. 17 is a top plan view of a perform of an alternative locking element of the present invention.

FIGS. 17 and 18 illustrate an alternative locking element 160 of the present invention. Locking element 160 functions similarly to locking element 60 of the embodiment of FIGS. 1–16. Locking element 160 includes a V-shaped body portion 161 comprising first and second radially extending walls 162 and 164 joined along a longitudinal axis. A first leg 166 extends proximally from the first wall and a second leg 168 extends proximally from the second wall. The legs flare outwardly with respect to the V-shaped body portion as shown in FIG. 18. Each of the legs 166 and 168 include a proximal end portion 170 and 172 that are angled toward one of the radially extending walls of the plunger rod assembly. Barbs 176 and 178 are integral with the first and second leg. The barbs face proximally and may be different in appearance from those illustrated in the drawings as long as they are capable of engaging the inside surface of the syringe barrel. A cutter or cutting edge 187 is positioned on the distal end of locking element 160. As with the embodiment of FIGS. 1–16, should an extraordinary force be used in an attempt to retract the plunger rod assembly, cutting edge 187 at the distal end of the locking element will penetrate the stopper rendering it unusable. The locking element is preferably formed of sheet metal. The locking element is preformed into the flat configuration illustrated in FIG. 17. The broken line show where folds will be made in the flat substrate 188 to form the locking element 160 illustrated in FIG. 18.

The syringe barrel employed in accordance with the invention may have a varying wall thickness along its length. The portion of the barrel used for containing medication could be relatively thin and resilient to ensure proper sealing with the stopper. The remainder of the barrel could be relatively thick and non-resilient such that it would tend to crack if squeezed by pliers or another device used for attempted tampering. Sufficient barrel crystallinity is desirable in the area of the locking element to cause this area to crack upon deformation of the syringe barrel to an extent that would permit retraction of the plunger rod assembly with the locking element.

Thus, it can be seen that the present invention provides a simple, reliable, easily fabricated, single use syringe which becomes inoperable or incapable of further use without any additional act on the part of the user and is capable of damaging the plunger rod stopper if excessive force is used in an attempt to re-use the syringe assembly.

What is claimed is:

1. A locking element for locking a syringe plunger rod having a stopper to a syringe barrel comprising:
    a body portion including a distal end portion and a proximal end portion;
    first means connected to said body portion for engaging a plunger rod;
    second means connected to said body portion for engaging a syringe barrel such that said locking element can slide distally with respect to the syringe barrel but is substantially prevented from sliding proximally within the syringe barrel; and
    a cutter attached to said distal end portion of said body portion for cutting a stopper.

2. The locking element of claim 1 wherein said second means for engaging includes a proximally extending barb.

3. The locking element of claim 2 wherein said body portion is generally V-shaped.

4. The locking element of claim 3 wherein said body portion, said first and second means for engaging, and said cutter are of integral construction.

5. The locking element of claim 4 including a first pair of legs extending from said proximal end portion of said body portion, said first means for engaging being connected to said legs.

6. The locking element of claim 5 including a first proximally extending barb adjacent said distal end portion of said body portion and a second proximally extending barb extending from at least one of said first pair of legs.

7. The locking element of claim 6 including a second pair of legs extending distally from said distal end portion of said body portion, each of said second pair of legs including a proximally extending barb and a cutting edge for cutting a stopper.

8. The locking element of claim 1 wherein said body portion, first and second means for engaging, and said cutter comprise an integral, resilient metal structure.

9. A syringe assembly comprising:
    a syringe barrel having an inside surface defining a chamber, an open end, and a distal end;
    a plunger rod assembly including an elongate body portion and a stopper connected to said elongate body portion;
    a locking element slidably positioned within said chamber, said locking element engaging said inside surface of said syringe barrel such that said locking element is substantially immovable in the direction of the open end of said syringe barrel, said locking element further being engageable with said plunger rod assembly such that said plunger rod assembly and locking element can be moved distally together toward the distal end of said syringe barrel, and
    a cutter connected to said locking element, said cutter being engageable with said stopper and capable of cutting said stopper upon attempted withdrawal of said plunger rod assembly from said chamber of said syringe barrel.

10. The syringe assembly of claim 9 wherein said locking element and cutter comprise an integral, resilient metal structure, said locking element being positioned such that said plunger rod assembly can be moved proximally with respect to said locking element.

11. The syringe assembly of claim 9 wherein said locking element includes one or more proximally extending barbs engaging said inside surface of said syringe barrel, and said locking element and stopper are positioned such that said plunger rod assembly can be moved proximally with respect to said locking element.

12. The syringe assembly of claim 11 wherein said locking element includes a body portion having a distal end and proximal end, said cutter being connected to said distal end, said body portion being generally V-shaped, and said elongate body portion of said plunger rod assembly includes a recess, said locking element extending into said recess.

13. The syringe assembly of claim 12 including a first pair of legs extending from and deflectable with respect to said proximal end of said body portion, said legs engaging said plunger rod assembly.

14. The syringe assembly of claim 13 including a first proximally extending barb adjacent said distal end of said body portion and a second proximally extending barb extending from at least one of said legs, said first and second barbs engaging said inside surface of said syringe barrel.

15. The syringe assembly of claim 13 including a second pair of legs extending distally from said distal end of said body portion, a proximally extending barb extending from each of said legs, said barbs engaging said inside surface of said syringe barrel, each of said second pair of legs including a cutting edge for cutting said stopper.

16. The syringe assembly of claim 9 wherein said elongate body portion of said plunger rod assembly includes a portion of reduced cross-sectional area configured to break upon the application of excessive bending or torsional force to said plunger rod assembly.

17. A locking element for locking a plunger rod having a stopper with respect to a syringe barrel, comprising:
    a generally V-shaped body portion including first and second walls connected to each other along a longitudinal axis;
    a first leg extending in a proximal direction from said first wall and having a portion extending at an angle with respect to said first wall;
    a first barb extending proximally from said first leg;
    a second leg extending proximally from said second wall and having a portion extending at an angle with respect to said second wall, each of said first and second legs being deflectable with respect to said body portion;
    a second barb extending proximally from said second leg;
    a distal end portion integral with said generally V-shaped body portion; and
    a cutting member on said distal end portion for cutting the stopper of a syringe plunger rod.

18. The locking element of claim 17 including a third barb extending proximally from said distal end portion.

19. The locking element of claim 18 including a fourth barb extending proximally from said distal end portion.

20. The locking element of claim 17 wherein said distal end portion includes third and fourth legs extending distally from said body portion, and a third barb extending from said third leg.

21. The locking element of claim 20 including a fourth barb extending proximally from said fourth leg.

22. The locking element of claim 21 wherein said first and second legs are substantially longer than the length of said body portion.

23. A syringe assembly comprising:
    a syringe barrel having an inside surface defining a chamber, an open end, and a distal end;
    a plunger rod assembly including an elongate body portion, a recess in said elongate body portion and a stopper connected to said elongate body portion;
    a locking element slidably positioned within said chamber, and extending within said recess, said locking element including:
        a generally V-shaped body portion including first and second walls connected to each other along a longitudinal axis;
        a first leg extending in a proximal direction from said first wall;
        a first barb extending proximally from said first leg and engaging said inside surface of said chamber;
        said first leg having a portion engageable with said plunger rod assembly;
        a second leg extending in a proximal direction from said second wall;
        a second barb extending proximally from said second leg and engaging said inside surface of said chamber;
        said second leg having a portion engageable with said plunger rod assembly;
        a distal end portion integral with said generally V-shaped body portion; and a cutting member on said distal end portion of said locking element for cutting said stopper.

24. The syringe assembly of claim 23 further including a third barb extending proximally from said distal end portion and engaging said inside surface of said syringe barrel.

25. The syringe assembly of claim 24 including a fourth barb extending proximally from said distal end portion of said locking element.

26. The syringe assembly of claim 23 wherein said plunger rod assembly includes ratchet teeth for engaging said first and second legs of said locking element.

27. The syringe assembly of claim 23 wherein said distal end portion of said locking element includes third and fourth legs extending distally from said body portion, and a third barb extending from said third leg.

28. The syringe assembly of claim 27 including a fourth barb extending proximally from said fourth leg of said locking element.

29. The syringe assembly of claim 28 wherein said first and second legs are substantially longer than the length of said body portion of said locking element.

30. The syringe assembly of claim 28 wherein each of said third and fourth legs includes a cutting edge for cutting said stopper.

31. A syringe assembly comprising:
   a syringe barrel having an inside surface defining a chamber, a proximal open end, and a distal end;
   a plunger rod assembly including an elongate body portion, a recess in said elongate body portion, a plurality of teeth formed on said elongate body portion and bounding said recess, said teeth defining a plurality of distally facing shoulders, and a stopper connected to said elongate body portion;
   a barrier within said recess and located proximally with respect to said teeth;
   a locking element slidably positioned within said chamber, and extending within said recess distally of said barrier, said locking element including:
   a generally V-shaped body portion including first and second walls connected to each other along a longitudinal axis;
   a first leg extending in a proximal direction from said first wall;
   said first leg having a portion engageable with at least one of said distally facing shoulders;
   a second leg extending in a proximal direction from said second wall;
   said second leg having a portion engageable with at least one of said distally facing shoulders;
   a distal end portion integral with said generally V-shaped body portion;
   at least one barb extending proximally from said locking element and engaging said inside surface of said syringe barrel; and
   a cutting member on said distal end portion for cutting said stopper.

32. The syringe assembly of claim 31 wherein each of said first and second legs include a barb extending proximally therefrom.

33. The syringe assembly of claim 31 wherein said first and second legs are substantially longer than the length of said body portion of said locking element.

34. The syringe assembly of clam 31 wherein said locking element includes third and fourth legs extending distally from said body portion, each of first and second legs including a proximally extending barb that engages said inside surface of said syringe barrel.

35. The syringe assembly of claim 34 wherein each of said third and fourth legs includes a cutting edge for cutting said stopper.

36. The syringe assembly of claim 31 wherein said elongate body portion of said plunger rod assembly includes a portion of reduced cross-sectional area configured to break upon the application of excessive bending or torsional force to said plunger rod assembly.

* * * * *